United States Patent [19]
Gordon et al.

[11] Patent Number: 6,100,099
[45] Date of Patent: Aug. 8, 2000

[54] TEST STRIP HAVING A DIAGONAL ARRAY OF CAPTURE SPOTS

[75] Inventors: Julian Gordon, Lake Bluff; Joanell Hoijer, Arlington Heights; Cynthia Jou, Libertyville; James Rhoads, Mundelein, all of Ill.

[73] Assignee: Abbott Laboratories, Abbott Park, Ill.

[21] Appl. No.: 09/181,245

[22] Filed: Oct. 28, 1998

Related U.S. Application Data

[62] Division of application No. 08/769,176, Dec. 18, 1996, Pat. No. 5,869,252, which is a continuation of application No. 08/302,646, Sep. 16, 1994, abandoned.

[51] Int. Cl.[7] ................................................. G01N 33/533
[52] U.S. Cl. .............................. 436/518; 422/56; 422/58; 422/60; 422/61; 435/7.1; 435/287.7; 435/287.8; 435/287.9; 436/518; 436/541; 436/807; 436/810
[58] Field of Search ................................ 422/56, 58, 60, 422/61; 435/7.1, 287.7, 287.8, 287.9; 436/518, 541, 807, 810

[56] References Cited

U.S. PATENT DOCUMENTS

| | | |
|---|---|---|
| 3,992,158 | 11/1976 | Przbylowicz et al. . |
| 4,094,647 | 6/1978 | Deutsch et al. . |
| 4,134,792 | 1/1979 | Boguslaski et al. . |
| 4,168,146 | 9/1979 | Grubb et al. . |
| 4,235,601 | 11/1980 | Deutsch et al. . |
| 4,298,688 | 11/1981 | Kallies . |
| 4,299,916 | 11/1981 | Litman et al. . |
| 4,328,183 | 5/1982 | Rosenfield et al. . |

(List continued on next page.)

FOREIGN PATENT DOCUMENTS

| | | |
|---|---|---|
| 0288737 | 11/1988 | European Pat. Off. . |
| 0323605 | 7/1989 | European Pat. Off. . |
| 0320308 | 8/1989 | European Pat. Off. . |
| 0336731 | 10/1989 | European Pat. Off. . |
| 0120602 | 1/1990 | European Pat. Off. . |
| 0357011 | 3/1990 | European Pat. Off. . |
| 0364255 | 4/1990 | European Pat. Off. . |
| 0164194 | 9/1990 | European Pat. Off. . |
| 0439182 | 7/1991 | European Pat. Off. . |
| 0191640 | 10/1991 | European Pat. Off. . |
| 0278220 | 11/1992 | European Pat. Off. . |
| 0281390 | 6/1994 | European Pat. Off. . |
| 0167366 | 4/1997 | European Pat. Off. . |
| 2099578 | 12/1982 | United Kingdom . |
| 8402721 | 7/1984 | WIPO . |
| 8607387 | 12/1986 | WIPO . |
| 8702774 | 5/1987 | WIPO . |
| 8808036 | 10/1988 | WIPO . |
| 8909835 | 10/1989 | WIPO . |
| 8912696 | 12/1989 | WIPO . |
| 9001069 | 8/1990 | WIPO . |

OTHER PUBLICATIONS

Barany, F., "Genetic disease detection and DNA amplificaiton using cloned thermostable ligase", *Proc. Natl. Acad. Sci. USA*, 88:189–193 (1991).

Bej, Asim, K., et al., "Amplification of Nucleic Acids by Polmerase Chain Reaction (PCR) and Other Methods and their Applications", *Critical Rev. in Biochem. And Mol. Biol.*, 26(3/4):301–334 (1991).

Birkenmeyer, L., et al., "Prelimanary Evaluation of the Ligase Chain Reaction for Specific Detection of *Neisseria gonnorrhoeae*", *Journ. Of Clin. Microbio.*, 30(12):3089–3094 (1992).

(List continued on next page.)

*Primary Examiner*—James C. Housel
*Assistant Examiner*—Bao-Thuy L. Nguyen
*Attorney, Agent, or Firm*—Paul D. Yasger

[57] ABSTRACT

The invention relates to multiplex ligase chain reaction (LCR). Two or more putative target sequences are selected. For each one, a set of four probes is used simultaneously to amplify the putative sequence if it is present in the sample. Preferably, all the amplicons are labeled with a common label/hapten and, for each different target, with a unique label/hapten. The invention also relates to an immunochromatographic strip device and method employing a diagonal array of capture spots.

2 Claims, 3 Drawing Sheets

U.S. PATENT DOCUMENTS

| | | |
|---|---|---|
| 4,358,535 | 11/1982 | Falkow et al. . |
| 4,361,537 | 11/1982 | Deutsch et al. . |
| 4,391,904 | 7/1983 | Litman et al. . |
| 4,425,438 | 1/1984 | Bauman et al. . |
| 4,435,504 | 3/1984 | Zuk et al. . |
| 4,517,288 | 5/1985 | Giegel et al. . |
| 4,563,419 | 1/1986 | Ranki et al. . |
| 4,588,555 | 5/1986 | Provonchee . |
| 4,787,963 | 11/1988 | MacConnell . |
| 4,806,311 | 2/1989 | Greenquist . |
| 4,855,225 | 8/1989 | Fung et al. . |
| 4,861,711 | 8/1989 | Friesen et al. . |
| 4,882,269 | 11/1989 | Schneider et al. . |
| 4,960,691 | 10/1990 | Gordon et al. . |
| 4,988,617 | 1/1991 | Landegren et al. . |
| 5,075,078 | 12/1991 | Osikowicz et al. . |
| 5,169,766 | 12/1992 | Schuster et al. . |
| 5,409,818 | 4/1995 | Davey et al. . |
| 5,422,252 | 6/1995 | Walker et al. . |
| 5,427,930 | 6/1995 | Birkenmeyer et al. . |
| 5,437,990 | 8/1995 | Burg et al. . |
| 5,480,784 | 1/1996 | Kacian et al. . |
| 5,486,452 | 1/1996 | Gordon et al. . |
| 5,605,794 | 2/1997 | Rust et al. . |
| 5,652,107 | 7/1997 | Lizardi et al. . |
| 5,981,298 | 11/1999 | Chudzile et al. . |

OTHER PUBLICATIONS

Birkenmeyer, L. G., et al., "DNA probe amplification methods", *Journ. Of Virol. Meth.*, 35:117–126 (1991).

Brownlee, et al., "Chromatography of P–Labelled Oligonucleotides on Thin Layers of DEAE–Cellulose", *European J. Biochem*, 11:395–399 (1969).

Chamberlain, J. S., et al., "Multiplex PCR for the Diagnosis of Duchenne Muscular Dystrophy", *PCR Protocols: A Guide to Methods and Applications*, 272–281 (1990).

Domedy, et al., "Gradient Thin–Layer Chromatography of Oligonucleotides on DEAE–Cellulose: An Alternative to Homochromatography", *Analytical Biochemistry*, 99:346–362 (1979).

Gordon, et al., Dot Immuno–Binding and Western Blotting as Diagnostic Tools, *Immunoenzymetic Techniques*, 303–306 (1983).

Hawkes, et al., "A Dot Immunobinding for Monoclonal and Other Antibodies", *Analytical Biochemistry*, 119(1):142–147 (1982).

Jeppesen, "The Nucleotide Sequences of Some Large Ribonuclease T Products from Bacteriophage R17 Ribonucleic Acid", *Biochem J.*, 124:357–366 (1971).

Jou, C., et al., "Deletion Detection in the Dystrophin Gene by Multiplex Gap Ligase Chain Reaction and Immunochromatographic Strip Technology", *Human Mutation*, 5:86–93 (1995).

Nickerson, D. A. et al., "Automated DNA diagnostics using an Elisa–based oligonucleotide ligation assay", *Proc. Natl. Acad. Sci. USA*, 8923–8927 (1990).

Rordorf, et al., A multidot Immunobinding Assay for Autoimmunity and the Demonstration of Novel Antibodies against Retroviral Antigens in the Sera of MRL Mice, *Journ of Immunological Methods*, 105–112 (1983).

Saiki, et al., "Genetic Analysis of Amplified DNA with Immobilized Seuqence–Specific Oligonucleotide Probes", *Proc. Natl. Acad. Sci. USA*, 86:6230–6234 (1989).

Steffan, R. J., "Polymerase Chain Reaction: Applications in Environmental Microbiology", *Annu. Rev. Microbiol.*, 45:137–61 (1991).

Towbin, H., et al., "Immunoblotting and Immunoblotting—current status and outlook", *Journ of Immun Mehtods*, 1–53 (1984).

Ursi, Jean–Paul, et al., "Utility of an internal control for the polymerase chain reaction", *APMIS*, 100:635–639 (1992).

Van Hamont, et al., "Quantitative Immunochromatographic Strip Assay Method and Apparatus", *Federal Register and the Patent and Trademark Official Gazette*, 1–21 (1985).

SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:1:

```
CACTGCGGGT TTTGCAGAAC AATAA                                          25
```

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 22

(xi) SEQUENCE DESCRIPTION: SEQ ID NO:2:

```
ATTGTTCTGC AAAACCCGCA GT                                             22
```

(2) INFORMATION FOR SEQ ID NO:3:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

(xi) SEQUENCE DESCRIPTION: SEQ ID NO:3:

```
GTAAGTAGTA CCCTGGACAA GGT                                            23
```

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:4:

```
GACCTTGTCC AGGGTACTAC TTACA                                          25
```

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CAAGTTTTGC CTCAACAAGT GAGCA                                             25

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

(xi) SEQUENCE DESCRIPTION: SEQ ID NO:6:

GCTCACTTGT TGAGGCAAAA CTT                                               23

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 22

(xi) SEQUENCE DESCRIPTION: SEQ ID NO:7:

GAAGCCATCC AGGAAGTGGA AA                                                22

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:8:

ATTTCCACTT CCTGGATGGC TTCAA                                             25

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

```
    (ix) FEATURE:
         (A) NAME/KEY: misc_feature
         (B) LOCATION: 1

(xi) SEQUENCE DESCRIPTION: SEQ ID NO:9:

TACATCCTTC TCAATGTCCA ATAGA                                          25

(2) INFORMATION FOR SEQ ID NO:10:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 23

(xi) SEQUENCE DESCRIPTION: SEQ ID NO:10:

CTATTGGACA TTGAGAAGGA TGT                                            23

(2) INFORMATION FOR SEQ ID NO:11:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 23

(xi) SEQUENCE DESCRIPTION: SEQ ID NO:11:

GCCCCCAAAT GCGAACATTC CAT                                            23

(2) INFORMATION FOR SEQ ID NO:12:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1

(xi) SEQUENCE DESCRIPTION: SEQ ID NO:12:

TATGGAATGT TCGCATTTGG GGGCA                                          25

(2) INFORMATION FOR SEQ ID NO:13:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
```

(B) LOCATION: 1

(xi) SEQUENCE DESCRIPTION: SEQ ID NO:13:

ACAGGCTGTC ACCACCACTC AGCCA                                                25

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

(xi) SEQUENCE DESCRIPTION: SEQ ID NO:14:

GGCTGAGTGG TGGTGACAGC CTA                                                  23

(2) INFORMATION FOR SEQ ID NO:15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

(xi) SEQUENCE DESCRIPTION: SEQ ID NO:15:

CACTAACACA GACAACTGTA ATG                                                  23

(2) INFORMATION FOR SEQ ID NO:16:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:16:

CCATTACAGT TGTCTGTGTT AGTGA                                                25

(2) INFORMATION FOR SEQ ID NO:17:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:17:

CGTGATAAGC TGACAGAGTG AAACA                                             25

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 24

(xi) SEQUENCE DESCRIPTION: SEQ ID NO:18:

GTTTCACTCT GTCAGCTTAT CACG                                              24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 24

(xi) SEQUENCE DESCRIPTION: SEQ ID NO:19:

GTTAAGGCTT GAAAGGGCAA GTAG                                              24

(2) INFORMATION FOR SEQ ID NO:20:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:20:

CTACTTGCCC TTTCAAGCCT TAACA                                             25

(2) INFORMATION FOR SEQ ID NO:21:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:21:

TTTTACCTGC AGGCGATTTG ACAGA                                             25

(2) INFORMATION FOR SEQ ID NO:22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

(xi) SEQUENCE DESCRIPTION: SEQ ID NO:22:

CTGTCAAATC GCCTGCAGGT AAA                                             23

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

(xi) SEQUENCE DESCRIPTION: SEQ ID NO:23:

CTGTTGAGAA ATGGCGGCGT TTT                                             23

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:24:

GAAAACGCCG CCATTTCTCA ACAGA                                          25

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:25:

TTGAATGCAA CTGGGGAAGA AATAA                                          25

(2) INFORMATION FOR SEQ ID NO:26:

```
     (i) SEQUENCE CHARACTERISTICS:
         (A) LENGTH: 22 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 22

(xi) SEQUENCE DESCRIPTION: SEQ ID NO:26:

ATTTCTTCCC CAGTTGCATT CA                                                22

(2) INFORMATION FOR SEQ ID NO:27:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 23

(xi) SEQUENCE DESCRIPTION: SEQ ID NO:27:

CAGCAATCCT CAAAAACAGA TGA                                               23

(2) INFORMATION FOR SEQ ID NO:28:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1

(xi) SEQUENCE DESCRIPTION: SEQ ID NO:28:

GCATCTGTTT TTGAGGATTG CTGAA                                             25

(2) INFORMATION FOR SEQ ID NO:29:

(i) SEQUENCE CHARACTERISTICS:
         (A) LENGTH: 25 base pairs
         (B) TYPE: nucleic acid
         (C) STRANDEDNESS: single
         (D) TOPOLOGY: linear (ii) MOLECULE TYPE: DNA (genomic)

(ix) FEATURE:
         (A) NAME/KEY: misc_feature
         (B) LOCATION: 1

(xi) SEQUENCE DESCRIPTION: SEQ ID NO:29:

AAGACCTTGA AGAGCAGTTA AATCA                                             25

(2) INFORMATION FOR SEQ ID NO:30:

(i) SEQUENCE CHARACTERISTICS:
         (A) LENGTH: 23 base pairs
         (B) TYPE: nucleic acid
```

```
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

(xi) SEQUENCE DESCRIPTION: SEQ ID NO:30:

GATTTAACTG CTCTTCAAGG TCT                                           23

(2) INFORMATION FOR SEQ ID NO:31:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

(xi) SEQUENCE DESCRIPTION: SEQ ID NO:31:

CTGCTGCTGT GGTTATCTCC TAT                                           23

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:32:

AATAGGAGAT AACCACAGCA GCAGA                                         25

(2) INFORMATION FOR SEQ ID NO:33:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:33:

CAAGTTATAA AATCACAGAG GGTGA                                         25

(2) INFORMATION FOR SEQ ID NO:34:

(i) SEQUENCE CHARACTERISTICS:
        (A) LENGTH: 23 base pairs
        (B) TYPE: nucleic acid
        (C) STRANDEDNESS: single
        (D) TOPOLOGY: linear
```

```
       (ii) MOLECULE TYPE: DNA (genomic)

(ix) FEATURE:
            (A) NAME/KEY: misc_feature
            (B) LOCATION: 23

(xi) SEQUENCE DESCRIPTION: SEQ ID NO:34:

CACCCTCTGT GATTTTATAA CTT                                            23

(2) INFORMATION FOR SEQ ID NO:35:

(i) SEQUENCE CHARACTERISTICS:
           (A) LENGTH: 23 base pairs
           (B) TYPE: nucleic acid
           (C) STRANDEDNESS: single
           (D) TOPOLOGY: linear (ii) MOLECULE TYPE: DNA (genomic)

(ix) FEATURE:
            (A) NAME/KEY: misc_feature
            (B) LOCATION: 23

(xi) SEQUENCE DESCRIPTION: SEQ ID NO:35:

GGTGGGTGAC CTTGAGGATA TCA                                            23

(2) INFORMATION FOR SEQ ID NO:36:

(i) SEQUENCE CHARACTERISTICS:
           (A) LENGTH: 25 base pairs
           (B) TYPE: nucleic acid
           (C) STRANDEDNESS: single
           (D) TOPOLOGY: linear (ii) MOLECULE TYPE: DNA (genomic)

(ix) FEATURE:
            (A) NAME/KEY: misc_feature
            (B) LOCATION: 1

(xi) SEQUENCE DESCRIPTION: SEQ ID NO:36:

TTGATATCCT CAAGGTCACC CACCA                                          25

(2) INFORMATION FOR SEQ ID NO:37:

(i) SEQUENCE CHARACTERISTICS:
           (A) LENGTH: 24 base pairs
           (B) TYPE: nucleic acid
           (C) STRANDEDNESS: single
           (D) TOPOLOGY: linear (ii) MOLECULE TYPE: DNA (genomic)

(ix) FEATURE:
            (A) NAME/KEY: misc_feature
            (B) LOCATION: 1

(xi) SEQUENCE DESCRIPTION: SEQ ID NO:37:

CCTGTGGGGC AAGGTGAACG TGGA                                           24

(2) INFORMATION FOR SEQ ID NO:38:

(i) SEQUENCE CHARACTERISTICS:
           (A) LENGTH: 22 base pairs
           (B) TYPE: nucleic acid
           (C) STRANDEDNESS: single
           (D) TOPOLOGY: linear (ii) MOLECULE TYPE: DNA (genomic)

(ix) FEATURE:
```

```
        (A) NAME/KEY: misc_feature
        (B) LOCATION: 22

(xi) SEQUENCE DESCRIPTION: SEQ ID NO:38:

CCACGTTCAC CTTGCCCCAC AG                                        22

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 22

(xi) SEQUENCE DESCRIPTION: SEQ ID NO:39:

GAAGTTGGTG GTGAGGCCCT GG                                        22

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:40:

CCCAGGGCCT CACCACCAAC TTCA                                      24

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:41:

GTGGAATCAC ACTGAGTGGA GA                                        22

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

TCTCCACTCA GTGTGATTCC AC                                        22
```

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 21

(xi) SEQUENCE DESCRIPTION: SEQ ID NO:43:

TCAACGAGCA AGAATTTCTT T                                        21

(2) INFORMATION FOR SEQ ID NO:44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:44:

AAAGAAATTC TTGCTCGTTG A                                        21

(2) INFORMATION FOR SEQ ID NO:45:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:45:

ATTCAATAAC TTTGCAACAG TG                                      22

(2) INFORMATION FOR SEQ ID NO:46:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 22

(xi) SEQUENCE DESCRIPTION: SEQ ID NO:46:

CACTGTTGCA AAGTTATTGA AT                                      22

(2) INFORMATION FOR SEQ ID NO:47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

AAGGAAAGCC TTTGGAGT                                                     18

(2) INFORMATION FOR SEQ ID NO:48:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:48:

ACTCCAAAGG CTTTCCTT                                                     18

(2) INFORMATION FOR SEQ ID NO:49:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:49:

GGCACCATTA AGAAAATAT CAT                                                23

(2) INFORMATION FOR SEQ ID NO:50:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

ATGATATTTT CTTTAATGGT GCC                                               23

(2) INFORMATION FOR SEQ ID NO:51:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 23

```
        (xi) SEQUENCE DESCRIPTION: SEQ ID NO:51:

TGGTGTTTCC TATGATGAAT ATA                                              23

(2) INFORMATION FOR SEQ ID NO:52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1

(xi) SEQUENCE DESCRIPTION: SEQ ID NO:52:

TATATTCATC ATAGGAAACA CCA                                              23
```

TEST STRIP HAVING A DIAGONAL ARRAY OF CAPTURE SPOTS

This a division of U.S. patent application Ser. No. 08/769,176, filed Dec. 18, 1996 now U.S. Pat. No. 5,869,252, which is a file-wrapper-continuation of abandoned U.S. Ser. No. 08/302,646 which application relates to amplification of DNA and, in particular, to the simultaneous amplification of multiple target sequences using the Ligase Chain Reaction (hereinafter "LCR"). It is a continuation-in-part of co-owned and co-pending U.S. Ser. No. 07/860,702 filed Mar. 31, 1992, which is incorporated by reference.

This application is related to several other applications relating to LCR, including U.S. Ser. No. 131,936 filed Dec. 11, 1987, now pending; a continuation of that application, U.S. Ser. No. 720,739 filed Jun. 25, 1991, now pending; U.S. Ser. No. 470,674 filed Jan. 26, 1990, now abandoned; and a continuation-in-part from that application, U.S. Ser. No. 634,771 filed Jan. 9, 1991; now pending. It is noted that published EP-A-320 308 corresponds to U.S. Ser. No 131,936, and published EP-A-439 182 corresponds to U.S. Ser. No. 634,771. Both of the published documents in their entirety are incorporated herein by reference.

BACKGROUND

LCR is a method for amplifying exponentially the number of detectable target molecules. It involves the use of two pairs of probes. A first or primary pair hybridizes with one strand of a target sequence at near-adjacent positions so that they can be ligated together in template-dependent fashion to form a reorganized primary molecule. The secondary pair is capable of hybridizing to the reorganized primary molecule. LCR was first described by Backman, et al. in EP-A-320 308. Much has been written about it since then. For example, see Wallace, EP-A-336 731; Orgel, WO 89/09835; Richards, WO 89/12696; Segev, WO 90/01069; and Barany, *Proc. Natl Acad Sci USA* 88:189–193 (1991). A variation of LCR known as "Gap" LCR is described in EP-A439 182 and in Segev, WO 90/01069.

Instead of using two pairs of probes capable of forming blunt-ended duplexes, at least one probe of one of the probe pairs initially includes a "modified" end which renders the resultant duplex "nonblunt" and/or not a suitable substrate for the ligase catalyzed fusion of the two probe duplexes. A "modified end" has either (1) a blocking moiety (or additional base residues) on a group (e.g. the 5' phosphate or the 3' hydroxyl) which, under ordinary LCR conditions, obligatorily participates in the ligase catalyzed fusion or (2) omitted bases to create a "gap" between one probe terminus and the next probe terminus In the "gap" embodiment, modified ends are created by eliminating from one or more of the probes a short sequence of bases, thereby leaving a recess or gap between the 5' end of one probe and the 3' end of the other probe when they are both hybridized to the target (or target complement, or polynucleotide generated therefrom). In order for LCR to amplify the target, the gaps between the probes must be filled in (i.e., the modification must be "corrected"). In a first version, this can be done using a polymerase or a reverse transcriptase and an excess of deoxynucleotide triphosphates which are complementary to the target strand opposite the gap. Alternatively, this can be done by supplying a fifth probe complementary to the target and a sixth probe complementary to the fifth probe.

PCR or polymerase chain reaction is a different method for amplifying DNA. It employs two primers which hybridize to opposite strands of a double stranded target. A polymerase initiates extension of the primer using the target as a template by sequentially adding the appropriate complementary nucleotides. PCR is described in U.S. Pat. Nos. 4,883,195 and 4,883,202, the entire disclosures of which are incorporated herein by reference.

PCR has been used in a multiplex manner to determine the presence of multiple target sequences in a single reaction. EP-A-364 255 describes the use of multiple primer sets to simultaneously amplify multiple target sequences by PCR. A similar disclosure is made in Chamberlain, et al., *Nucl. Acids Res.*, 16:1141–56 (1988).

In addition, Nickerson, et al., *Proc. Natl. Acad. Sci. USA*, 87:8923–8927 (1990) proposes an oligonucleotide ligation assay ("OLA") for multiple target sequences, pending the development of "multiple, nonisotopic reporter groups". OLA employs two contiguous probes that are ligated together and the ligated product is detected as a measure of the presence of a target sequence.

In spite of the existence of these disclosures, multiplex LCR is not available in the hands of the public. The art does not provide sufficient guidance actually to enable the concept of multiplex LCR. This is due largely to the inapplicability of PCR conditions to LCR.

SUMMARY OF THE INVENTION

Accordingly, we have now demonstrated the feasibility of multiplex LCR with as many as seven different probe sets. In one aspect, the invention is a method for performing LCR amplification simultaneously on two or more target sequences. The method comprises the steps of:

a. providing a reaction solution containing nucleic acid of a sample as single-stranded nucleic acid, said sample putatively having one or more of a plurality of target nucleic acid sequences;

b. for each putative target sequence, providing in the reaction solution at least four nucleic acid probes (a probe set), wherein: i) the first and second of said probes are primary probes, and the third and fourth of said probes are secondary nucleic acid probes; ii) the first probe is a single strand capable of hybridizing to a first segment of a primary strand of the target nucleic acid; iii) the second probe is a single strand capable of hybridizing to a second segment of said primary strand of the target nucleic acid; iv) the 5' end of the first segment of said primary strand of the target is positioned relative to the 3' end of the second segment of said primary strand of the target to enable joining of the first probe to the second probe when said probes are hybridized to said primary strand of said target nucleic acid, thus forming a reorganized primary molecule having a first portion and a second portion; v) the third probe is capable of hybridizing to a first portion of the reorganized primary molecule; and vi) the fourth probe is capable of hybridizing to a second portion of the reorganized primary molecule, the first portion of the reorganized primary molecule being positioned relative to the second portion of the reorganized primary molecule to enable joining of the third probe to the fourth probe when said third and fourth probes are hybridized to said reorganized primary molecule, thus forming a reorganized secondary molecule; and wherein for each putative target sequence said probe set is provided at a concentration that enables said joining in the presence of each of the other probe sets; and c. repeating the following cycle:
  i) hybridizing said probes with nucleic acid in said sample;
  ii) performing said joining to form said reorganized molecules; and
  iii) denaturing nucleic acid in said sample;
  whereby with successive cycles the quantity of reorganized primary and secondary molecules is increased for each putative target sequence present in the reaction solution.

In the usual case, the joining is performed by a ligase enzyme, or a ligase enzyme and a polymerase enzyme. Usually, the cycle of step c is repeated from 10 to 100 times, preferably from 20 to about 60 times.

Generally, the amplification product is detected by means of a unique detectable label associated with each probe set, each of said detectable labels being differentiable from the others. Labels preferably include specific binding members, such as haptens or polynucleotides. The labels can be used for either detection, or separation or both. In a preferred configuration, each of the probe sets are labeled with two distinct labels such that the reorganized molecules, when hybridized together, are labeled with two labels, at least one of which is a unique label and the other label is a common label, the same for each probe set.

In a preferred protocol, the common label is used for detection and the unique label is used to separate the reorganized molecules of one probe set from the reorganized molecules of at least one other probe set. Separation may be accomplished by different binding locations on a single solid phase, or by using a solid phase which is characterized by a property which permits differentiation of one from another.

In a second aspect, the invention is a method of detecting the presence, absence or quantity of each of a plurality of target nucleic acid sequences by a multiplex ligase chain reaction comprising the steps of:
  a. providing a reaction solution containing nucleic acid of a sample as single-stranded nucleic acid, said sample putatively having one or more of a plurality of target nucleic acid sequences;
  b. for each putative target sequence, providing in the reaction solution a set of at feast two and optionally four nucleic acid probes (a probe set), wherein: i) the first and second of said probes are primary probes, and the optional third and fourth of said probes are secondary nucleic acid probes; ii) the first probe is a single strand capable of hybridizing to a first segment of a primary strand of the target nucleic acid; iii) the second probe is a single strand capable of hybridizing to a second segment of said primary strand of the target nucleic acid; iv) the 5' end of the first segment of said primary strand of the target is positioned relative to the 3' end of the second segment of said primary strand of the target to enable joining of the first probe to the second probe when said probes are hybridized to said primary strand of said target nucleic acid, thus forming a reorganized primary molecule having a first portion and a second portion; v) the third probe is capable of hybridizing to a first portion of the reorganized primary molecule; and vi) the fourth probe is capable of hybridizing to a second portion of the reorganized primary molecule, the first portion of the reorganized primary molecule being positioned relative to the second portion of the reorganized primary molecule to enable joining the third probe to the fourth probe when said third and fourth probes are hybridized to said reorganized primary molecule, thus forming a reorganized secondary molecule;

wherein at least one probe of each probe set contains a detectable label, the detectable label associated with each probe set being differentiable from the detectable labels associated with the other probe sets, whereby the presence, absence or quantity of each putative target sequence can be determined; and wherein for each putative target sequence said probe set is provided at a concentration that enables said joining in the presence of each of the other probe sets; and c. performing the following cycle:
  i) hybridizing said probes with nucleic acid in said sample;
  ii) performing said joining to form said reorganized molecules; and
  iii) denaturing nucleic acid in said sample;
  whereby with each cycle the quantity of reorganized primary and, optionally, secondary molecules is increased for each putative target sequence present in the reaction solution; and d. measuring the detectable label associated with each of said probe sets as a measure of the presence or quantity of target nucleic acid in the reaction solution.

The same variations of labeling, separation and detection mentioned above are useful for this aspect of the invention.

Finally, the invention relates to an immunochromatographic device and method for multiplex detection of multiple analytes. The device comprises a strip of porous material capable of tansporting fluids by capillary action, said strip having at least first and second unique capture reagents immobilized thereon in first and second discrete spots spaced apart from an end used to contact transport fluid, said unique first and second capture reagents being specific different first and second analytes, respectively, wherein said second discrete spot is spaced from said first discrete spot in both vertical and horizontal dimensions, vertical being the direction of fluid flow. Preferably, the device contains three or more discrete spots, and said spots are all spaced from one another in both vertical and horizontal dimensions to form a substantially linear, diagonal array of spots.

The method of using the device involves contacting said contact end with a test solution suspected to contain the analyte under conditions that allow said solution to be transported by capillary action at least to the most distal capture spot; and determining for each capture spot, whether analyte became bound to said capture spot.

The method and device are useful for conventional specific binding analytes, such as antigens and antibodies, as well as for polynucleotide analytes.

DETAILED DESCRIPTION

Figure 1:
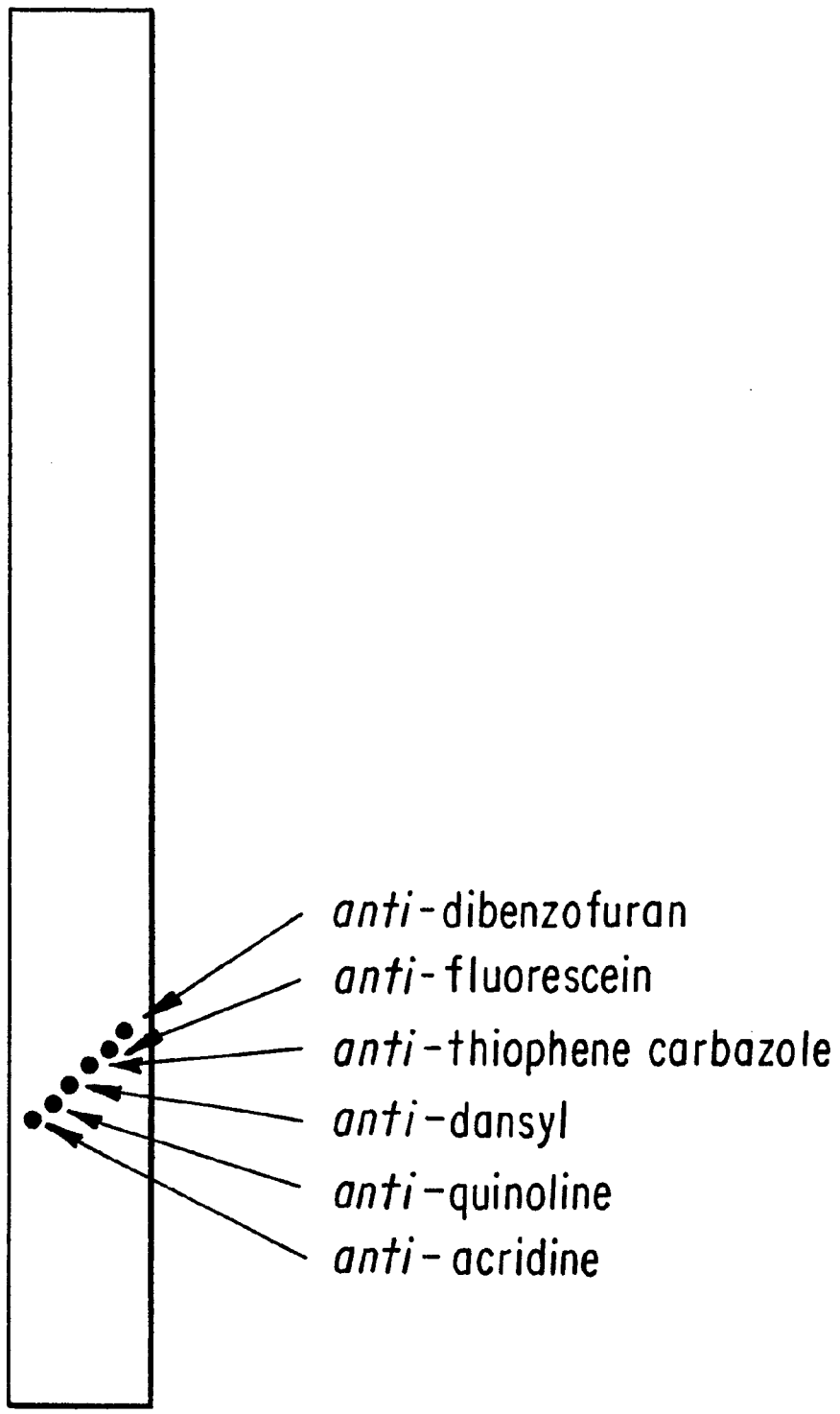
FIG. 1 is a diagram of the immunochromatography strip used in multiplex LCR detection.

As used in this application, a "multiplex" process refers to the carrying out of a method or process simultaneously and in the same reaction vessel on two or more, typically three or more, different target sequences. Thus, multiplex LCR is the performance of LCR on a plurality of targets using at least one set of four probes for each putative target sequence. In like manner, the term "N-plex" LCR, where N is a numeral, refers to LCR performed to amplify or detect one or more of N target sequences.

A "target sequence" or "target nucleic acid" is a segment of nucleic acid (DNA or RNA) The segment may be from about 10 or 15 to several hundred nucleotides in length. For LCR, a target segment is usually about 30 to about 60 nucleotides and the sequence is known. A target is "putative" if its presence is expected or anticipated, or if it or a variation of it is expected or anticipated. For example, in multiplex LCR of a homozygote to determine which of two mutually exclusive alleles is present, the sequences surrounding both alleles are putative target sequences, even though it is known that only one is expected to be present The possible alternatives for each allele are all putative targets.

The step of "joining" as recited above encompasses several known methods of joining two probes together. The preferred method is by the use of a thermostable ligase, although other ligases and other ligating agents are not excluded. Ligases are discussed in the incorporated EP-A-320 308 and in EP-A-373 962 which is also incorporated by reference. Joining is also possible by chemical means or by photoligation. Joining also encompasses the possible intermediate step of "correcting" a modified end as taught in the incorporated EP-A-439 182. Correction includes the filling of a gap with an extending reagent (such as polymerase) as well as the cleaving of a blocking group (such as with endonuclease IV).

A reaction solution is typically prepared by collecting the sample from a patient and disrupting the cells to release the DNA or RNA. Detergents may be used, but other known methods of sample preparation are also included. Specific buffer compositions are available from the literature, and from the examples. The DNA or RNA is rendered single-stranded by altering the stringency conditions, usually by heating.

The probes for multiplex LCR are generally no different than the probes for conventional LCR. However, to facilitate detection at least one probe of each probe set should bear a detectable label. Moreover, the detectable labels from each of the probe sets must all be differentiable, one from the other, either by signal differentiation or by spatial differentiation. As is described in more detail below, signal differentiation refers to the ability to distinguish targets in essentially the same location (i.e homogeneous assay) by virtue of differences in the signal (e.g. different fluorescent emission wavelengths or different colors). By contrast, spatial differentiation refers to the ability to distinguish targets based on the position or location of the signal. Spatial differentiation is also known as separation and may be accomplished by size, molecular weight, charge density, or magnetic or specific binding properties, and the like. Of course, it is possible and often desirable to utilize both types of differentiation within the same system.

Where separation is preferred in order to interpret the results, a preferred embodiment uses two labels: at least one of which is a unique or differentiable label. The other label may be common, and shared by each of the probe sets, or it may be unique as well. Depending on the particular protocol used (see below), either the common label or the unique label may be used for detection, and the other label may be used for separation.

The term "label" refers to a molecule or moiety having a property or characteristic which is capable of detection. A label may be directly detectable, as with radioisotopes, fluorophores or chemilumiphores; or a label may be indirectly detectable, as with haptens or polynucleotide tails. When indirect labels are used for detection or signalling purposes, they are used in conjunction with a signalling entity complex. A "signalling entity" is a molecule or moiety which provides the detectable property or characteristic. The signalling entity may be direct, as with a colloidal particle (e.g. colloidal gold or selenium); or it may be indirect, as with an enzyme (e.g. alkaline phosphatase, β-galactosidase or horseradish peroxidase). Indirect signalling entities may require additional components, e.g. substrate, as is well known in the art. The "signalling entity complex" includes a signalling entity conjugated to specific binding partner, such as an antibody or polynucleotide. Such conjugates may be prepared according to any known method of conjugation.

Useful labels include radioisotopes, especially as the common label. However, it may be possible to use a radioisotope as a unique label when the radiation can be differentiated. Likewise, fluorophores and chemilumiphores are best used as common labels, although it would be possible to use them as unique labels if their signal can be differentiated (e.g. on the basis of wavelength). A hapten, polynucleotide or other specific binding member may also serve as the common label, although the ability to easily distinguish one specific binding member from another renders them ideally suited for the unique label. When different specific binding members are employed, conjugates bearing different specific binding partners are used according to one of the protocols described below.

Many different haptens are known, and vitually any hapten can be used with the present invention. The invention requires only that a specific binding partner is known or can be prepared (a definitional property of "hapten") and that the hapten can be coupled to the probe such that it does not interfere with hybridization. Many methods of adding haptens to probes are known in the literature. Enzo Biochemical (New York) and Clontech (Palo Alto) both have described and commercialized probe labelling techniques. For example, a primary amine can be attached to a 3' oligo end using 3'-Amine-ON CPG™ (Clontech, Palo Alto, Calif.). Similarly, a primary amine can be attached to a 5' oligo end using Aminomodifier II® (Clontech). The amines can be reacted to various haptens using conventional activation and linking chemistries.

In addition, co-pending applications U.S. Ser. Nos. 625, 566, filed Dec. 11, 1990 and 630,908, filed Dec. 20, 1990 teach methods for labelling probes at their 5' and 3' ends respectively. Both the aforementioned co-pending applications are incorporated by reference. Some illustrative haptens include many drugs (eg. digoxin, theophylline, phencyclidine (PCP), salicylate, etc.), T3, biotin, fluorescein (FITC), dansyl, 2,4-dinitrophenol (DNP); and modified nucleotides such as bromouracil and bases modified by incorporation of a N-acetyl-7-iodo-2-fluorenylamino (AIF) group; as well as many others. Certain haptens described herein are disclosed in co-pending, co-owned U.S. patent applications Ser. No. 07/808,508 (adamantaneacetic acids), U.S. Ser. No. 07/808,839 (carbazoles and dibenzofurans), both filed Dec. 17, 1991, U.S. Ser. No. 07/858,929 (acridines), and U.S. Ser. No. 07/858,820 (quinolines), both filed Mar. 27, 1992 (collectively referred to herein as the "hapten applications"). The entire disclosure of each of the above hapten applications is incorporated herein by reference.

It should be understood that the number of probes necessary for multiplex amplification or detection is generally four times the number of putative sequences. In the case of an assay for "N" different bacterial organisms, the number of probes required is 4×N. In the case of genetic testing of mutations, the rule of 4×T probes, where T is the number of putative targets, is still the general or usual case. However, certain exceptions are described below. It should be kept in mind that, depending on the type and complexity of the mutation, there may be several putative targets for each mutation. Take for example, a simple, single base substitution. If it is known that the substitution is always one type of base, the possible putative target sequences are two: the wild type and the mutation substitution. However, if it is known that any of the four bases can substitute at the locus, then the putative target sequences become four. The general rule requires eight (4×T, T=2) probes in the first case; and 16 (4×T, T=4) probes in the second.

The general rule of four probes for each putative target will hold regardless of the type and complexity of the mutation. However, in some simple mutations two probes from one set (say, arbitrarily, the right two) will also serve as the two (right) probes from the other sets and fewer than 4×T probes will be required. These simple mutations include any small deletion, insertion or substitution the ends of which are known with certainty. So long as the ends are known, the size of the deletion, insertion or change does not affect its characteization as "simple". With these "simple" mutations, the number of probes required is (2T+2). The +2 is the common probe set on one side of the mutation, while the 2T represents all the possible permutations of the mutation, i.e all the possible putative target sequences. Of course, the number of possible permutations depends on the nature of the mutation.

Another "special case" where less than 4T probes are required is possible where the mutation configuration of the gene is such that two mutations are near enough to one another that a common probe can be used between the two mutations, with specialized probes on the outside ends. "Near enough" in this context means within a distance that can be spanned by an LCR probe. Typically, that distance is about 20 to 40 bases.

Interpretation of LCR results may include looking at the number of cycles required to produce target and background curves that are distinguishable from one another. For a given concentration of probes, the background signal will develop after n cycles, while the target signal develops after only t cycles. In order for LCR to be useful as a diagnostic tool, it is desired that n be far greater than t; i.e. that there be as large a "cycle window" as possible between target and background, see, e.g. EP-A-320 308. It has also been shown that the cycle number at which signal "comes up" varies with probe concentration: The higher the probe concentration, the sooner the signal comes up, and vice versa. As a consequence, it has been discovered that it is preferable to balance the probe concentration carefully in multiplex LCR Since all reactions are run for the same number of cycles, all target signals must "come up" at approximately the same time. This can be insured by carefully balancing the concentration of each probe set so that each reaction reaches peak or at least detectable signal levels at approximately the same cycle number. It is impossible to predict precisely how to adjust probe concentration for a given probe set, but this can readily be determined empirically through simple experiments.

It is generally known that the melt temperature of the probe sets for LCR should be approximately equal. However, it has been discovered in multiplex LCR that the melt temperatures may vary by as much as 8 to 10° C. from one side to the other.

Other reaction conditions for multiplex LCR are similar to those used for more fundamental LCR. The same buffer, pH and salt conditions are generally acceptable. However, it is desirable to add a somewhat higher concentration of ligase, as shown in the examples. In addition, if gap filling LCR is used, additional polymerase may be desired as well.

As mentioned above, the most preferred protocols include two labels, a common label and a unique label. Either may serve as the detection label. For simplicity, the embodiments are described using haptens as both the common and unique labels. It is, of course, understood that another label is easily substituted for at least one of the haptens, especially the common hapten.

According to a preferred standard LCR protocol, a first hapten is used to capture and separate the reorganized molecules. A second hapten is used to couple the reorganized complex with the signalling entity. This procedure is described more completely in EP-A-439 182. For example a fluorescein moiety is attached to the 5' end of the first primary probe and to the 3' end of the first secondary probe. In addition, a different hapten, say biotin, is attached to the 3' end of the second primary probe and to the 5' end of the second secondary probe. Thus, when the reorganized molecules are duplexed, two biotins are found at one end of the duplex and two fluoresceins are found at the other end. A solid phase having a coating of anti-fluorescein is used to separate reorganized molecules from unligated probes having biotins. (Unligated probes having fluoresceins are also captured.) The separated complexes are detected by using avidin or anti-biotin labeled with a detectable signalling entity such as an enzyme.

For multiplex LCR this system of separation and detection need only be slightly modified. It is still possible to use just one hapten common to all probe sets at one end (detection or capture) of the reorganized molecules. Only the other end of the molecules needs to be differentiable, e.g. via a unique hapten. Two distinct protocols are possible.

First, the common hapten (say, biotin) could be used to capture all the reorganized molecules. Then the different complexes can be differentiated by using specific haptens, and anti-hapten conjugates with differentiable signalling entities. For example (paying attention to the orientation and proper probe end considerations mentioned above) probes for target A are labeled with biotin and fluorescein; probes for target B are labeled with biotin and dansyl; and probes for target C are labeled with biotin and digoxin. All reorganized molecules (and biotinylated probes) are captured on a solid phase. Anti-fluorescein coupled to colloidal gold produces a reddish brown color if target A is present; anti-dansyl coupled to colloidal selenium produces a pinkish color if target B is present and anti-digoxin coupled to polypyrrole latex produces a black color if target C is present. As an alternative, the antibodies can be coupled to different enzymes (eg. alkaline phosphatase, peroxidase, β-galactosidase) the substrates or products of which produce different colors.

Since discerning different colors on a single solid phase may be difficult, a second and more preferred protocol involves using the common hapten/label as the detection function and using the unique hapten to separate the targets from one another on one or more solid phases. For example, beads or microparticles which can be physically separated (eg. by manipulation, filtration, chromatography, sedimentation, centrifugation, magnetic field, etc.) may be used as a solid phase. Separable groups of these solid phases are each coated with antibody against one of the unique haptens. After multiplex LCR and incubation with the solid phases, the groups are separated and a common signalling entity complex is reacted with the common hapten. Different sequences are determined by the appearance of signal on one or more of the different solid phase groups.

A dot-blot method is also useful to separate reorganized molecules. To discrete locations on a sheet-like solid phase are immobilized antibodies to the several unique haptens. Incubation of this sheet with the reaction solution will permit separation of the reorganized molecules, based on the specificity of the antibodies for the unique haptens. Again, the common hapten is employed with a signalling entity conjugate to generate signal at any location which contains a reorganized molecule. The solid phase is interpreted based on the location (and optionally the intensity) of the signal.

A variation of this technique employs immunochromatography to separate the reorganized molecules on the basis of the unique hapten. Rather than incubate the solid phase with the reaction solution, the solid phase is a porous chromatographic material and the reaction solution wicks through it, drawn by capillary action. A preferred porous material is nitrocellulose. As with the dot-blot method, antibody to each unique hapten is immobilized at various locations throughout the strip, preferably along a diagonal line. When the reaction solution carrying all the reorganized molecules encounters an immobilized antibody spot, the reorganized molecules bearing the complementary hapten are "captured" and immobilized at that location. This technique is a variation of the technique described in EP-A-357 011, the entire disclosure of which (and particularly those aspects relating to immunochromatographic detection of target nucleic acid) is incorporated by reference. The following examples demonstrate this technique.

It has been found that the immunochromatography method works best when the capture spots for various polynucleotide targets (and even regular analytes) are aligned in a diagonal configuration as shown in FIG. 1. It is desirable to spatially separate capture spots in both dimensions for several reasons. First, vertical separation is useful to better differentiate signals from adjacent spots. However, if the spots are spaced only in this dimension, there is a tendency for label to accumulate at the first positive capture spot. Spots downstream from this spot are "shadowed" and generally do not develop signal as readily. Thus, it is preferred to separate spots in a horizontal direction as well. Spots spaced only in a horizontal direction would require a much wider strip in order to achieve the resolution necessary to read the strip.

In yet another variation of either protocol the reorganized molecules can be separated and/or detected by sequence-specific probe hybridization instead of haptens. This variation is possible with the separable groups of solid phases, with the sheet-like solid phase and with the chromatographic medium. The only difference is that, instead of immobilizing a unique hapten-specific antibody on the solid phase, a hybridization probe is immobilized, the probe being specific for sequences found in the first primary and or first secondary probes (ie. the same probes which carried the unique hapten in the prior variation). The method of chromatographic medium specific hybridization is described further in EP-A-387 696, the entire disclosure of which (and particularly those aspects relating to immunochromatographic detection of analytes) is incorporated herein by reference.

The multiplex LCR method of the present invention has numerous applications, depending on the type of target employed. First, it is useful in genetic screening or testing. Often a particular genetic disease or trait manifests itself as a mutation or change in the genetic code at one or a finite number of locations in the genome. Some diseases or conditions (e.g. sickle cell anemia, phenylketonuria, Tay-Sachs disease, medium chain acyl CoA dehydrogenase deficiency, cystic fibrosis) manifest themselves as a point mutation of a single base in the DNA. Others (e.g. cystic fibrosis, Duchene's Muscular Dystrophy (DMD)) can manifest themselves by short alterations or deletions in one or a relatively small number of exon locations. The ability to do multiplex LCR permits the simultaneous analysis of an individual's DNA at each of the exons where deletions/ alterations are known to be causative for a particular disease.

Another use for multiplex LCR is in the diagnosis of certain bacterial or viral diseases which typically occur from many variant strains of an infecting organism or virus. For example, human papilloma virus (HPV) types 6, 8, 11, 16, 18, 31, and 33 are all known to exist. Universal or consensus probes and primers will amplify all HPV regardless of type. However, only types 16, 18 and possibly 33 are of significant clinical interest due to their association with cancerous lesions. Thus, a multiplex LCR assay permits the simultaneous type-specific amplification of each variant. This gives the clinician additional information not available from simple universal amplification or from simple type-specific amplification of one type. This approach is also useful for HIV, which has at least two known types; and for *Chlamydia trachomatis*, which has at least 15 serovars.

It may also be useful to perform multiplex LCR when only a single organism is of interest. For example, multiple target sequences may be picked for confirmation or improved specificity. For example, sequences from both the MOMP gene and the cryptic plasmid might be selected to detect *C.trachomatis* DNA. Alternatively, internal controls might be run by including probes that will amplify β-globin sequences, as well as probes that will amplify the desired target.

Another use for multiplex LCR is in identity testing. A panel of perhaps 10 or more sequences may be selected which are highly variant in the general population. By determining the presence or absence of each of these sequences, an individual may be "typed" with a unique pattern of presence or absence of each particular exon sequence. In a binary format, individual "A" is identified as "0111001001", while individual "B" is identified as "0000111011", where a "0" indicates the absence of a particular exon sequence and a "1" indicates the presence of a particular exon sequence.

Other uses will be readily apparent to those skilled in this art.

EXAMPLES

The invention will be more completely understood with reference to the following examples which are intended to be illustrative only, and do not limit the invention. Throughout the examples the following abbreviations have the meanings given.

BSA refers to bovine serum albumin.

EPPS refers to a buffer of N-(2-hydroxyethyl)piperazine-N'-(3-propanesulfonic acid).

NAD refers to nicotinamide adenine dinucleotide, an energy source for certain biological reactions.

PCR refers to the polymerase chain reaction

TRIS refers to tris-(hydroxymethyl)aminomethane buffer.

TTP refers to thymidine triphosphate, one of the substrates for polymerase.

Abbott TestPack Plus™ is a trademark of Abbott Laboratories used to designate a chromatographic or wicking type of immunoassay. This assay format is described in further detail in EP-A-421 294 and EP-A-357 011, as well as in other literature.

Example 1

Oligo Synthesis and Haptenation
Part A—Sequence and Synthesis:

The following oligonucleotides (see Table 1) were synthesized following established procedures using β-cyanoethylphosphoramidites on a model 380A DNA synthesizer (Applied Biosystems, Foster City Calif.), where x=primary amine derived from 3'-Amine-ON CPG™ (Clontech, Palo Alto, Calif.), y=primary amine derived from Aminomodifier II® (Clontech), p=phosphate derived from Phosphate-ON® (Clontech), and A,C,G, and T have their usual meanings. Probes are written 5' to 3' from left to right. Melting temperatures are given for probe pairs as follows: first and second hybridize, and third and fourth hybridize.

*predicts a rod shaped cytoskeletal protein.* Cell 53, 219–228 (1988). According to the same numbering scheme, oligos 5–8 are specific for a portion of exon 8 of the Duchenne Muscular Dystrophy gene; oligos 9–12 am specific for a portion of exon 12 of the DMD gene; oligos 13–16 are specific for a portion of exon 17 of the DMD gene: oligos 17–20 are specific for a portion of exon 19 of the DMD gene; oligos 21–24 are specific for a portion of exon 44 of the DMD gene; oligos 25–28 are specific for a portion of exon 45 of the DMD gene; oligos 29–32 are specific for a portion of exon 48 of the DMD gene; and oligos 33–36 are specific for a portion of exon 51 of the DMD gene. Oligos 37–40 are specific for a portion of the human β-globin gene and are used as a control.

TABLE 1

| Sequence ID No | SEQUENCE | Melt Temp (° C.) | DMD Exon No. |
|---|---|---|---|
| 1. | yCACTGCGGGT TTTGCAGAAC AATAA | | |
| 2. | pATTGTTCTGC AAAACCCGCA GT-thiophene carbazole | | 4 |
| 3. | pGTAAGTAGTA CCCTGGACAA GGTx | | |
| 4. | yGACCTTGTCC AGGGTACTAC TTACA | | |
| 5. | CAAGTTTTGC CTCAACAAGT GAGCA | | |
| 6. | pGCTCACTTGT TGAGGCAAAA CTT-dansyl | | 8 |
| 7. | pGAAGCCATCC AGGAAGTGGA AAx | | |
| 8. | yATTTCCACTT CCTGGATGGC TTCAA | | |
| 9. | yTACATCCTTC TCAATGTCCA ATAGA | | |
| 10. | pCTATTGGACA TTGAGAAGGA TGT-quinoline | | 12 |
| 11. | pGCCCCCAAAT GCGAACATTC CATx | | |
| 12. | yTATGGAATGT TCGCATTTGG GGGCA | | |
| 13. | yACAGGCTGTC ACCACCACTC AGCCA | | |
| 14. | pGGCTGAGTGG TGGTGACAGC CTA-quinoline | 74° | 17 |
| 15. | pCACTAACACA GACAACTGTA ATGx | | |
| 16. | yCCATTACAGT TGTCTGTGTT AGTGA | 66° | |
| 17. | yCGTGATAAGC TGACAGAGTG AAACA | | |
| 18. | pGTTTCACTCT GTCAGCTTAT CACG-dibenzofuran | 69° | 19 |
| 19. | pGTTAAGGCTT GAAAGGGCAA GTAGx | | |
| 20. | yCTACTTGCCC TTTCAAGCCT TAACA | 68° | |
| 21. | yTTTTACCTGC AGGCGATTTG ACAGA | | |
| 22. | pCTGTCAAATC GCCTGCAGGT AAAx | | 44 |
| 23. | pCTGTTGAGAA ATGGCGGCGT TTTx | | |
| 24. | yGAAAACGCCG CCATTTCTCA ACAGA | | |
| 25. | yTTGAATGCAA CTGGGGAAGA AATAA | | |
| 26. | pATTTCTTCCC CAGTTGCATT CA-dansyl | 66° | 45 |
| 27. | pCAGCAATCCT CAAAAACAGA TGAx | | |
| 28. | yGCATCTGTTT TTGAGGATTG CTGAA | 67° | |
| 29. | yAAGACCTTGA AGAGCAGTTA AATCA | | |
| 30. | pGATTTAACTG CTCTTCAAGG TCT-thiophene carbazole | | 48 |
| 31. | pCTGCTGCTGT GGTTATCTCC TATx | | |
| 32. | yAATAGGAGAT AACCACAGCA GCAGA | | |
| 33. | yCAAGTTATAA AATCACAGAG GGTGA | | |
| 34. | pCACCCTCTGT GATTTTATAA CTTx | 65° | 51 |
| 35. | pGGTGGGTGAC CTTGAGGATA TCAx | | |
| 36. | yTTGATATCCT CAAGGTCACC CACCA | 70° | |
| 37. | acridine-CCTGTGGGGC AAGGTGAACG TGGA | | human β globin gene |
| 38. | pCCACGTTCAC CTTGCCCCAC AG-acridine | | |
| 39. | pGAAGTTGGTG GTGAGGCCCT GGx | | |
| 40. | yCCCAGGGCCT CACCACCAAC TTCA- | | |

Oligos 1–4 are specific for a portion of exon 4 of the Duchenne Muscular Dystrophy (DIMD) gene, following the numbering scheme described by Koenig M, Monaco A P, and Kunkel, L M. in *The complete sequence of dystrophin*

Part B—Haptenation

The 3'-end of some oligonucleotides were conjugated with haptens, as indicated in Table 1. The conjugation of these haptens followed standard β-cyanoethyl-- phosphoramidite chemistry, and is described in the aforementioned hapten applications. A similar procedure is described for fluorescent label conjugates in published U.S. application NTIS ORDER No. PAT-APPL-7-246,688) (Cohen, et al., 1989). The structures of the haptens used are shown in Table 2, below:
TABLE 2
| Hapten | Structure |
|---|---|
| acridine | 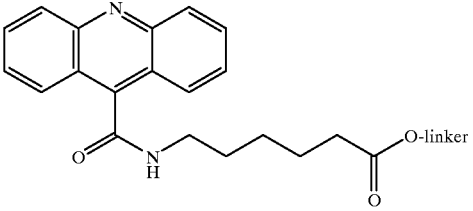 |
| dansyl | 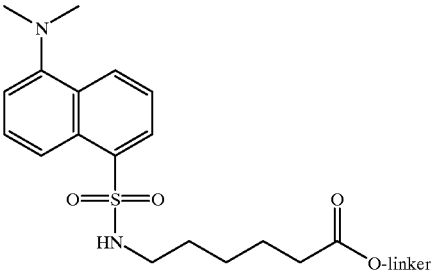 |
| dibenzofuran | 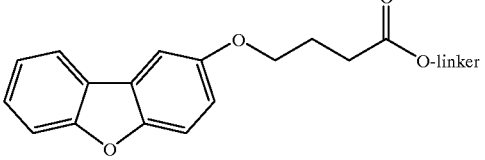 |
| fluorescein | 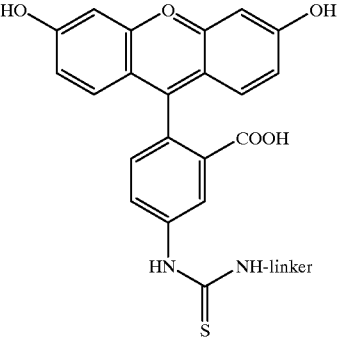 |
| quinoline | 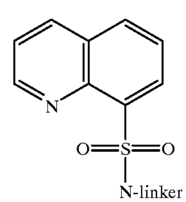 |

TABLE 2-continued

| Hapten | Structure |
|---|---|
| thiophene carbazole | (structure: carbazole with N-sulfonyl-thiophene and O-linker with butanoate) |

All oligonucleotides were purified by reversed-phase HPLC to remove failure sequences and, in the case of haptenated oligos, any unhaptenated species.

Example 2

Biotinylation

The aminated ends of oligos 3, 4, 7, 8, 11 12, 15, 16, 19, 20, 23, 24, 27, 28, 31, 32, 35, 36, 39, and 40 from example 1 were labeled with biotin essentially following the protocol of Urdea, et. al., *Nucl. Acids Res.*, 16(11):4937–4956 (1988). Briefly, up to 1 mg oligo was dissolved in 100 µL of 0.1 M sodium phosphate buffer, pH 7.5, and treated with 2 mg biotin-(aminocaproyl)2-N-hydroxysuccinimide ester in 100 µL dimethylformamide (DMF) for 16 hours at room temperature.

Oligos 22 (3' end) and 33 (5' end) were linked to fluorescein after synthesis by dissolving up to 1 mg oligo in 100 µL of 0.1 M sodium borate buffer, pH 9.0, and treating with 2 mg of fluorescein isothiocyanate (FTTC) for 15 hours at room temperature. Alternatively, the 3' aminated end of oligo 34 could be reacted with FITC, rather than haptenating oligo 33.

All biotin- and fluorescein-labeled oligonucleotides were purified by column chromatography through Sephadex® G-25 (Pharmacia, Piscataway N.J.), preparative gel electrophoresis, and ethanol precipitation.

For quality control purposes, the integrity of reorganized molecules after performing LCR was monitored on the IMx® instrument (Abbott Labs) using the typical biotin/fluorescein bihaptenated complex as taught in EP-A-439 182. For this reason, oligos 1, 9, 13, 17, 21, 25 and 29 were synthesized with a 5' primary amine. Portions of these oligos were reacted with fluorescein, as above, to provide the biotin/fluorescein complex necessary for IMx analysis. However, when used in multiplex LCR, the unhaptenated, aminated oligos were used.

Example 3

LCR Reaction Conditions

The labeled oligos of example 2 were used, in various combinations, in "gap filling" modified LCR essentially as described in EP-A-439 182. In general, the following reagents were mixed in a 0.5 mL polypropylene tube:

| Reagent | Final Concentration |
|---|---|
| water | (to give a final volume of 45 µL) |
| reaction buffer | 15 mM EPPS pH 7.8 |
| | 20 mM KCl |
| | 30 mM MgCl$_2$ |
| oligonucleotides | see TABLE 3 |
| NAD | 0.1 mM |
| TTP | 1 µM |
| sample | 250 ng DNA |
| mineral oil | 2 drops/tube |

The mixture was heated at 100° C. for 3 minutes, cooled, and the following were added in a volume of 5 µL, to give a final reaction volume of 50 µL:

| Reagent | Final Concentration |
|---|---|
| DNA ligase from *Thermus thermophilus* | 3400 U/50 µL |
| DNA polymerase from Thermus (MBR Inc., Milwaukee WI) | 1.2 U/50 µL |

The mixture was then subjected to 37 cycles of programmed temperature change, the cycle being 85° C. for 30 seconds and 45° C. for 20 seconds. The thermal cycling was carried out in a TempCycler™ (Coy Laboratory Products, Ann Arbor Mich.).

TABLE 3

| To Detect This Exon | Use These Oligos | At These Concentrations (number of molecules of each oligo per reaction tube (50 µL)) |
|---|---|---|
| Exon 4 | 1–4 | $1.5 \times 10^{12}$ |
| Exon 8 | 5–8 | $7.7 \times 10^{11}$ |
| Exon 12 | 9–12 | $3.8 \times 10^{11}$ |
| Exon 17 | 13–16 | $7.7 \times 10^{11}$ |
| Exon 19 | 17–20 | $7.7 \times 10^{11}$ |
| Exon 44 | 21–24 | $3.8 \times 10^{11}$ |
| Exon 45 | 25–28 | $3.8 \times 10^{11}$ |
| Exon 48 | 29–32 | $3.1 \times 10^{11}$ |
| Exon 51 | 33–36 | $3.8 \times 10^{11}$ |
| β-globin | 37–40 | $7.7 \times 10^{11}$ |

Example 4

Antibodies and Solid Phase

Antiserum was raised in rabbits against immunogens prepared from conjugates of hapten and either bovine serum albumin (BSA) or keyhole limpet hemocyanin (KLH). The preparation and description of these sera is described in the above-mentioned hapten applications, although any known procedure for raising antibodies would suffice. These sera were purified by passage through protein A Sepharose® (Pharmacia).

Antiserum against dansyl was a mouse monoclonal obtained from the University of Pennsylvania (Fan, S-T. and Karush, F. *Molecular Immunology* 21:1023–1029 (1984)).

These antisera were diluted in 0.1 M TRIS pH 7.8, 0.9% NaCl, 0.1% BSA, 1% sucrose, and a trace of phenol red. Portions (0.2 µL) of these diluted antisera were spotted in a regular pattern (see FIG. 1) onto strips of nitrocellulose (Schleicher and Schuell AE 98, 5 µm) of dimensions approximately 4×50 mm. The concentrations of antisera were as indicated in Table 4.

TABLE 4

| antiserum against | concentration (mg/mL) |
|---|---|
| acridine | 2.55 |
| dansyl | 0.5 |
| dibenzofuran | 3.4 |
| fluorescein | 0.5 |
| quinoline | 0.75 |
| thiophene carbazole | 0.25 |

Example 5

Label Conjugate

Colloidal selenium was prepared following the procedure of Yost, D. A. et. al. (U.S. Pat. No. 4,954,452 (1990)). The colloid was diluted in water to achieve an optical density of 16 at 545 nm. To 1 mL of this suspension was added 1 µL of antibiotin (Abbott Laboratories) at 1 mg/mL and 60 µL of BSA at 100 mg/mL. This mixture was mixed on a vortex mixer for 1 minute.

Example 6

Multiplex Immunochromatography

The LCR reaction mixtures of Example 3 were analyzed by Abbott TestPack Plus™ immunochronatography essentially following the protocol of EP-A-357 011. Briefly, the colloidal suspension of Example 5 (15 µL) was diluted with buffer (14 µL; 0.1 M TRIS pH 7.8, 0.9% NaCl. 3% alkali-treated casein) and mixed with the product of the LCR reaction (1 µL). A nitrocellulose strip of Example 4 was admitted to the suspension. After 5 minutes, the chromatography process was complete, and the nitrocellulose strip was removed from the reaction/colloid suspension and allowed to dry. The presence of a colored spot at the locus of antibody application indicated the presence of a specific LCR product.

Example 7

Analysis or Patient Samples for DMD

Samples of human DNA obtained from patients with Duchenne Muscular Dystrophy were analyzed for the presence of exons 4, 12, 17, 19, 44, 45, 48, and 51 using oligos 1–4 and 9–36. Oligos 37–40 were included in the reaction mix as a procedural control to detect the presence of human DNA. The analysis of each sample was performed in two parts: in one reaction tube was the mixture described in Example 3 containing oligos 13–28 and 33–40 (to amplify exons 17, 19, 45, 48, and 51; along with human β-globin); and in another tube was the LCR reaction mix containing oligos 1–4, 9–12, 29–32, and 37–40 (to amplify exons 4, 12, and 44; along with human β-globin). These analyses were performed by subjecting the sample DNA to LCR following Example 3, and subsequently immunochromatography of the resulting mix following Example 6.

Figure 2A:
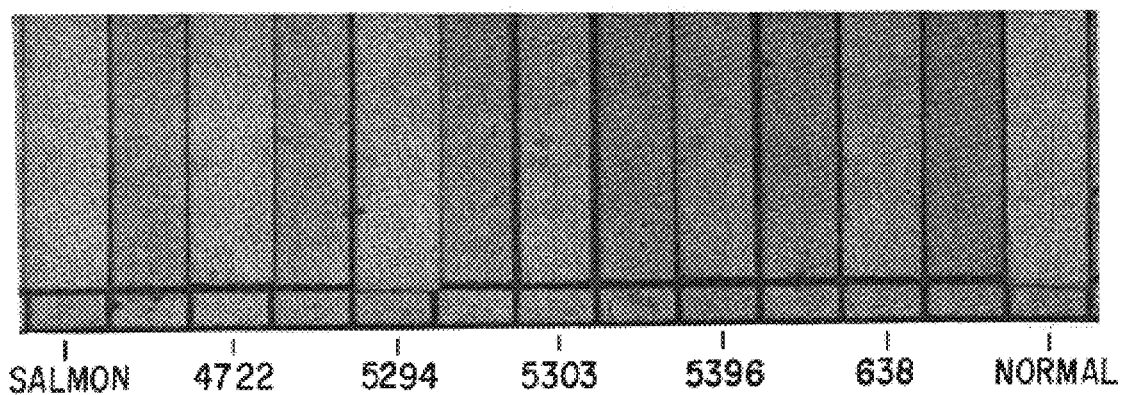
FIGS. 2a and 2b are photographs showing the immunochromatographic strip results of multiplex LCR performed on patient samples from example 7.
Figure 2B:
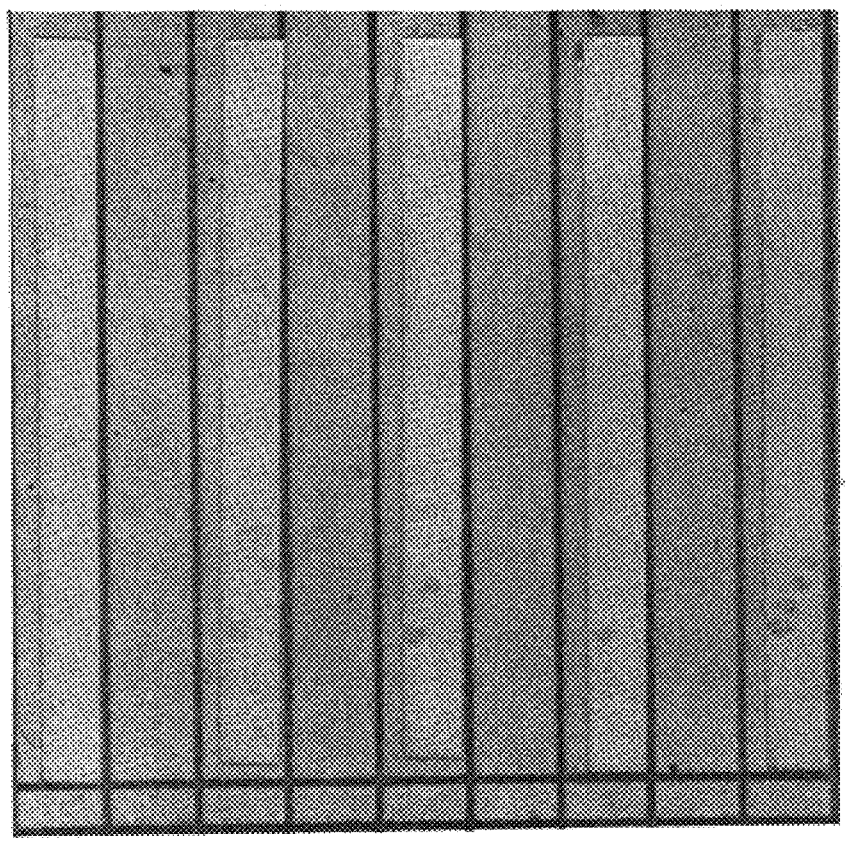

In FIG. 2 are shown photographs of nitrocellulose strips after immunochromatography. The photograph of FIG. 2a shows 7 nitrocellulose strips. These show the presence of amplification products specific for (spots from bottom to top) human β-globin, and DMD exons 17, 45, 48, 51, and 19. The samples contained 250 ng of DNA from, respectively (from left to right): salmon sperm DNA; 5 individual patients suffering from Duchenne Muscular Dystrophy (patient numbers indicated in the photograph), and normal human DNA. Similarly, the photograph of FIG. 2b shows 5 nitrocellulose strips. These show the presence of amplification products specific for (spots from bottom to top) human β-globin, and DMD exons 12, 4, and 44. The samples contained 250 ng of DNA from, respectively (from left to right): salmon sperm DNA; 3 individual patients suffering from Duchenne Muscular Dystrophy (patient numbers not indicated in the photograph—these are (from left to right) patients 5294, 4036, and 638), and normal human DNA.

The missing exons for each patient are known from PCR (see Table 5).

TABLE 5

| Patient Number | Exons Deleted (by PCR) all others will be amplified |
|---|---|
| 4722 | 17, 19, 45, 48, and 51 (44 not tested) |
| 5294 | 4, 12, 17 and 19 |
| 5303 | 45 |
| 5396 | 51 |
| 638 | 4, 12, 17, 19, 44, and 45 |
| 4036 | 12 and 44 (17, 19, 45, 48, and 51 not tested) |

Example 8

Oligo Synthesis for Cystic Fibrosis

The following oligonucleotides (see Table 6) were synthesized following established procedures using β-cyanoethylphosphormidites on a model 380A DNA synthesizer (Applied Biosystems, Foster City Calif.), where p=phosphate derived from Phosphate-ON® (Clontech), biotin is introduced using Biotin-ON® (Clontech), and A,C,G, and T have their usual meanings. Probes are written 5' to 3' from left to right. Haptentation as indicated was performed as described in Example 1.

TABLE 6

| Sequence ID No. | SEQUENCE | CF mutation |
|---|---|---|
| 41. | Dansyl-GTGGAATCAC ACTGAGTGGA GA | G551D |
| 42. | pTCTCCACTCA GTGTGATTCC AC | |
| 43. | pTCAACGAGCA AGAATTTCTT T-biotin | |
| 44. | biotin-AAAGAAATTC TTGCTCGTTG A | |
| 45. | biotin-ATTCAATAAC TTTGCAACAG TG | W1282χ |
| 46. | pCACTGTTGCA AAGTTATTGA AT-biotin | |
| 47. | pAAGGAAAGCC TTTGGAGT | |
| 48. | thioph.-carb.-ACTCCAAAGG CTTTCCTT | |
| 49. | fluorescein-GGCACCATTA AAGAAAATAT CAT | ΔF508 |
| 50. | pATGATATTTT CTTTAATGGT GCC | |
| 51. | pTGGTGTTTCC TATGATGAAT ATA-biotin | |
| 52. | biotin-TATATTCATC ATAGGAAACA CCA | |

Example 9

LCR Reaction Conditions

The labeled oligos of example 8 were used for blunt LCR essentially as described in EP-A-320-308 using the following concentrations of reagents:

| Reagent | Final Concentration |
|---|---|
| water | (to give a final volume of 45 μL) |
| reaction buffer | 50 mM EPPS pH 7.8 |
| | 150 mM KCl |
| | 10 mM MgCl$_2$ |
| oligonucleotides 41, 42, 43, and 44 | 3.3 × 10$^{11}$ copies of each |
| oligonucleotides 45, 46, 47, and 48 | 4.2 × 10$^{11}$ copies of each |
| oligonucleotides 49, 50, 51, and 52 | 2.7 × 10$^{11}$ copies of each |
| NAD | 0.1 mM |
| BSA | 5 μg |
| sample | 250 ng DNA |
| mineral oil | 2 drops/tube |

The mixtures were heated at 100° C. for 3 minutes, cooled to room temperature, and the following were added in a volume of 5 μL:

| Reagent | Final Concentration |
|---|---|
| DNA ligase from *Thermus thermophilus* | 3400 U/50 μL |

The mixture was then subjected to 45 cycles of programmed temperature change, this cycle being 85° C. for 30 seconds and 57° C. for 20 seconds. The thermal cycling was carried out in a TempCycler™ (Coy Laboratory Products, Ann Arbor Mich.).

Example 10

Analysis of Patient Samples for Cystic Fibrosis Mutations

Samples of human DNA obtained from patients with Cystic Fibrosis were analyzed for the presence of mutations G551D, W1282X, and ΔF508 using oligos 41–52. These analyses were performed by subjecting the sample DNA to LCR following Example 9, and subsequent immunochromatography of the resulting mix following Example 6. Reagents were prepared as before (see Examples 4–6).

Figure 3:
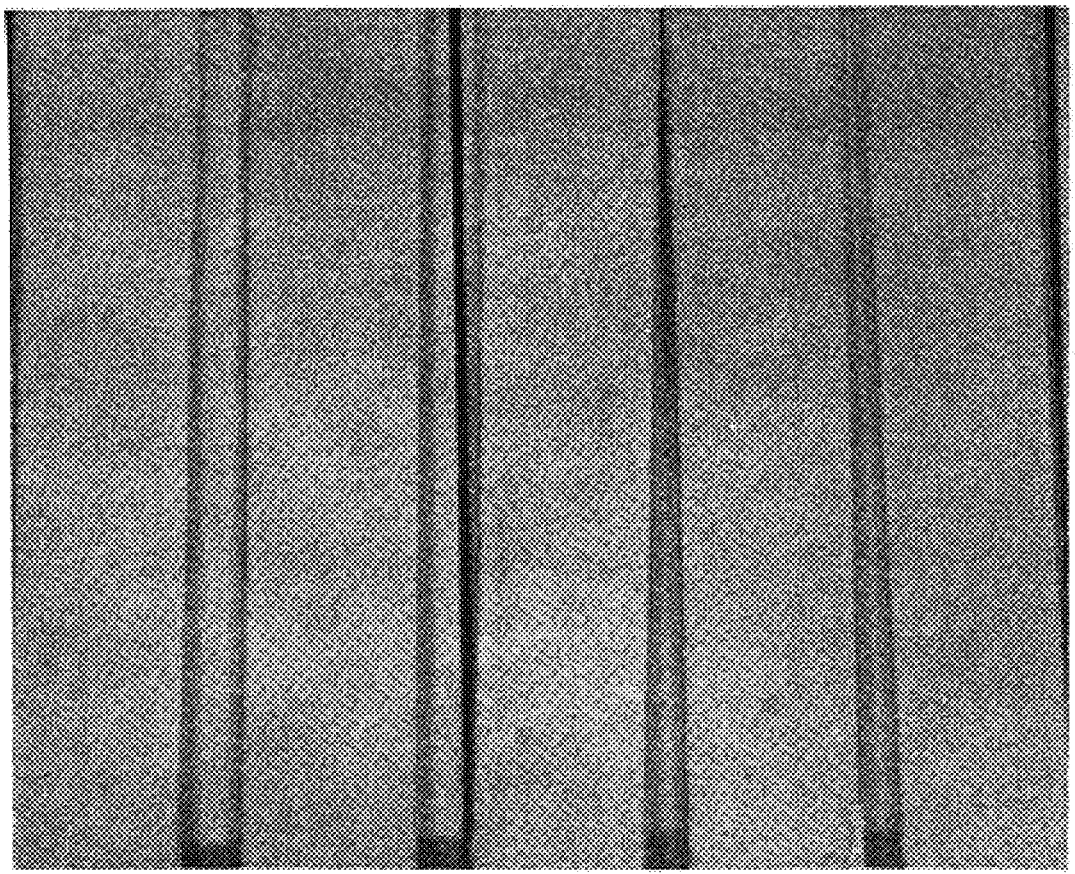
FIG. 3 is a photograph showing the immunochromatographic strip results of multiplex LCR performed on patient samples from example 10.

In FIG. 3 is shown a photograph of nitrocellulose strips after immunochrmatography. It shows the presence of amplification products specific for (spots from bottom and left to top and right) CF mutations W1282X, ΔF508, and G551D. The samples were: 1) water (no DNA), 2) patient heterozygous for G542X mutation, 3) patient heterozygous for W1282X mutation, 4) patient heterozygous for ΔF508 mutation, and 5) patient heterozyg3us for G551D mutation. No spot appears after amplification of water or G542X DNA (strips 1 and 2). Only one spot appears on strip 3, and this is located near the left of the strip (locus of anti-thiophene-carbazole immobiization), indicating a positive amplification of only the W1282X DNA. Only one spot appears on strip 4, and this is near the middle of the strip (locus of anti-fluorescein immobilization), indicating a positive amplification of only ΔF508 DNA. Only one spot appears on strip 5, and this is located near the right of the strip/locus of anti-dansyl immobilization), indicating a positive amplification of only G551D DNA.

Although all 12 oligos were present in all the reaction tubes, permitting the amplification of DNA from all three mutations, only the specific DNA present in each sample actually was amplified Each patient was heterozygous for their particular mutation, meaning that each also carried one normal gene. In no case was the normal gene shown to be amplified by any of the oligonucleotides.

What is claimed is:

1. An immunochromatographic device for multiplex detection of multiple analytes, comprising a strip of porous material capable of transporting fluids by capillary action, said strip having at least first and second unique capture reagents immobilized thereon in first and second discrete spots spaced apart from an end used to contact transport fluid, said unique first and second capture reagents being specific different first and second analytes, respectively, wherein said second discrete spot is spaced from said first discrete spot in both vertical and horizontal dimensions to form a substantially linear, diagonal array of spots, vertical being the direction of fluid flow.

2. The device of claim 1 wherein three or more discrete spots are provided, and said spots are all spaced from one another in both vertical and horizontal dimensions to form a substantially linear, diagonal array of spots.

* * * * *

UNITED STATES PATENT AND TRADEMARK OFFICE
CERTIFICATE OF CORRECTION

PATENT NO.    : 6,100,099
DATED         : August 8, 2000
INVENTOR(S)   : Julian Gordon et al.

It is certified that error appears in the above-identified patent and that said Letters Patent is hereby corrected as shown below:

<u>Title page,</u>
Item [75], Inventors replace "Joanell" with -- Joenell --.

Signed and Sealed this

Fourth Day of December, 2001

Attest:

*Nicholas P. Godici*

NICHOLAS P. GODICI
*Attesting Officer*    *Acting Director of the United States Patent and Trademark Office*